US010245140B2

(12) United States Patent
Haddock et al.

(10) Patent No.: US 10,245,140 B2
(45) Date of Patent: Apr. 2, 2019

(54) INTRAOCULAR DEVICE WITH ARTICULATED HOUSING STRUCTURES

(71) Applicant: Verily Life Sciences LLC, Mountain View, CA (US)

(72) Inventors: Joshua Naaman Haddock, Mountain View, CA (US); Dimitri Azar, Chicago, IL (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

(21) Appl. No.: 14/985,311

(22) Filed: Dec. 30, 2015

(65) Prior Publication Data
US 2017/0189169 A1 Jul. 6, 2017

(51) Int. Cl.
*A61F 2/16* (2006.01)
*A61F 2/14* (2006.01)

(52) U.S. Cl.
CPC .............. *A61F 2/1624* (2013.01); *A61F 2/14* (2013.01); *A61F 2002/1681* (2013.01); *A61F 2250/0001* (2013.01); *A61F 2250/0002* (2013.01); *A61F 2250/0004* (2013.01); *A61F 2250/006* (2013.01)

(58) Field of Classification Search
CPC ............ A61F 2/1624; A61F 2250/0001; A61F 2250/0002; A61F 2/14
USPC ........................ 623/4.1, 6.22, 6.43; 607/54
See application file for complete search history.

(56) References Cited

U.S. PATENT DOCUMENTS

| | | | | |
|---|---|---|---|---|
| 6,312,393 B1 * | 11/2001 | Abreu | .................. | A61B 3/1241 600/558 |
| 6,847,847 B2 * | 1/2005 | Nisch | ........................ | A61F 2/14 607/54 |
| 8,197,539 B2 * | 6/2012 | Nasiatka | .................. | A61F 9/08 607/54 |
| 8,834,566 B1 * | 9/2014 | Jones | .................... | A61F 2/1624 623/6.22 |

(Continued)

FOREIGN PATENT DOCUMENTS

WO  WO 2007/051171 A2  5/2007
WO  WO 2011/008846 A1  1/2011

OTHER PUBLICATIONS

PCT/US2016/062303—International Search Report and Written Opinion, dated Feb. 14, 2017, 11 pages.

(Continued)

*Primary Examiner* — David H Willse
*Assistant Examiner* — Javier Blanco
(74) *Attorney, Agent, or Firm* — Christensen O'Connor Johnson Kindness PLLC (57) ABSTRACT

Techniques and mechanisms to facilitate implantation of an ophthalmic device in an eye. In an embodiment, the ophthalmic device includes multiple housing structures (housings), where components of the ophthalmic device are variously disposed in respective ones of such housings. The housings are flexibly coupled each to a respective other one of such housings. One or more flexible interconnects of the device allow for articulation of the housings during implantation in an eye. In another embodiment, first circuitry disposed in one housing facilitates operation of the ophthalmic device to sense a condition at the eye or to assist sight with the eye. Second circuitry, disposed in another of the housings, is electrically coupled with the first circuitry via a flexible interconnect.

12 Claims, 6 Drawing Sheets

(56) References Cited

U.S. PATENT DOCUMENTS

| | | |
|---|---|---|
| 8,886,334 B2 | 11/2014 | Ghaffari et al. |
| 9,044,316 B2 | 6/2015 | Fehr et al. |
| 2007/0100443 A1 | 5/2007 | Peyman |
| 2007/0260307 A1 | 11/2007 | Azar |
| 2008/0086206 A1* | 4/2008 | Nasiatka .................. A61F 9/08 623/6.14 |
| 2009/0287275 A1* | 11/2009 | Suaning .................. A61F 9/08 607/54 |
| 2010/0103369 A1* | 4/2010 | Pugh ...................... A61F 9/023 351/158 |
| 2010/0152848 A1 | 6/2010 | Williamson et al. |
| 2011/0015733 A1* | 1/2011 | Schnell ................ A61F 2/1616 623/6.18 |
| 2013/0073038 A1* | 3/2013 | Azar ...................... A61F 2/147 623/6.22 |
| 2013/0190867 A1* | 7/2013 | Peyman ................ A61F 2/1635 623/6.13 |
| 2013/0338767 A1* | 12/2013 | Mazzocchi ........... A61F 2/1635 623/6.22 |
| 2014/0192313 A1 | 7/2014 | Riall et al. |
| 2014/0192314 A1 | 7/2014 | Riall et al. |
| 2015/0148648 A1 | 5/2015 | Pugh |
| 2017/0172731 A1* | 6/2017 | Mattes .................. A61F 2/1624 |

OTHER PUBLICATIONS

U.S. Appl. No. 14/937,135, filed Nov. 10, 2015, Haddock, Joshua N.

* cited by examiner

INTRAOCULAR DEVICE WITH ARTICULATED HOUSING STRUCTURES

BACKGROUND

1. Technical Field

This disclosure relates generally to ophthalmic devices, and in particular but not exclusively, relates to accommodating intraocular lenses.

2. Background Art

Accommodation is a process by which the eye adjusts its focal distance to maintain focus on objects of varying distance. Accommodation is a reflex action, but can be consciously manipulated. Accommodation is controlled by contractions of the ciliary muscle. The ciliary muscle encircles the eye's elastic lens and, when contracted, relieves tension applied to the lens via the zonules, causing the lens to relax, change shape, and thus alter its optical power.

As an individual ages, the effectiveness of the ciliary muscle degrades. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide today (110 million in the United States alone) and that number is expected to substantially rise as the world's population ages.

Recent technologies have begun to provide for various devices that operate in or on a human eye to aid the visual focus of a user. For some types of these devices, an accommodating lens includes one or more elements and circuitry to apply an electrical signal to change a focusing power of the one or more elements. As successive generations of integrated circuitry continue to scale down in size and power consumption, there is expected to be an increased demand for additional functionality to be incorporated in medical devices such as accommodation-capable (or other) ophthalmic implants. Meeting this demand is constrained by the size of the human eye, which limits the amount of space available for an intraocular device to provide communication, sensor, power and/or other functionality.

BRIEF DESCRIPTION OF THE DRAWINGS

The various embodiments of the present invention are illustrated by way of example, and not by way of limitation, in the figures of the accompanying drawings and in which.

DETAILED DESCRIPTION

Embodiments described herein variously provide for an implantable ophthalmic device that comprises multiple, flexibly coupled sections. Rather than encasing all components a single vessel, implantable ophthalmic devices according to some embodiments variously distribute components across multiple sections (referred to herein as "housings") that are flexibly coupled to one another. Such sections may be coupled to one another electrically via one or more flexible interconnects that, for example, are made from or are disposed in a biocompatible material. The electrical couplings may include, for example, metal wires embedded in medical grade silicone and/or flex circuits fabricated from biocompatible materials. In allowing for articulation between housings of an ophthalmic device, some embodiments facilitate implantation of the device in an eye through an incision that is relatively small—e.g., comparable to incisions required for implantation of conventional intraocular devices.

Certain features of various embodiments are described herein with reference to an ophthalmic device that provides different levels of accommodation to aid sight with an eye. However, some embodiments are not limited to the providing of automatic accommodation, and such description may be extended to additionally or alternatively apply to any of a variety of other implantable ophthalmic devices. For example, a device according to another embodiment may provide only one level of accommodation. In another embodiment, an implantable device includes one or more sensors to detect a condition (e.g., a level of pressure) in or on the eye—e.g., in addition to, or in lieu of, the device aiding sight by the eye.

Ophthalmic devices discussed herein may comprise multiple portions or segments, referred to herein as "housings", that are coupled to one another via one or more flexible (e.g., semi-rigid) connectors. Flexibility of the one or more connectors may allow for movement (articulation) of housings relative to one another. A housing may be a rigid structure that surrounds—e.g., in at least a two dimensional plane—one or more components that are to aid in detection of a condition of an eye and/or to aid in sight with the eye. Such components may include circuitry, optics, one or more sensors and/or the like. A housing may hermetically seal some or all such components. In one embodiment, a housing is itself an optical structure that, for example, has formed therein a dynamic focusing optic (or "dynamic optic"). Alternatively, a housing may form an aperture that extends around the perimeter of an optical structure, forming a seal.

An exterior of an ophthalmic device according to one embodiment may include respective surfaces of multiple articulated housings. Such surfaces may be formed by one or more biocompatible materials that accommodate implantation of the ophthalmic device in a human (or other) eye. Examples of some materials that may be used include, but are not limited to, any of various biocompatible hydrogels, silicones, hydrophobic acrylics, fluorinated polymethacrylates and/or the like. In an embodiment, one or more housings include a coating of biocompatible material that, for example, is formed by atomic layer deposition. Such materials may be adapted from those used in existing intraocular devices, for example.

In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
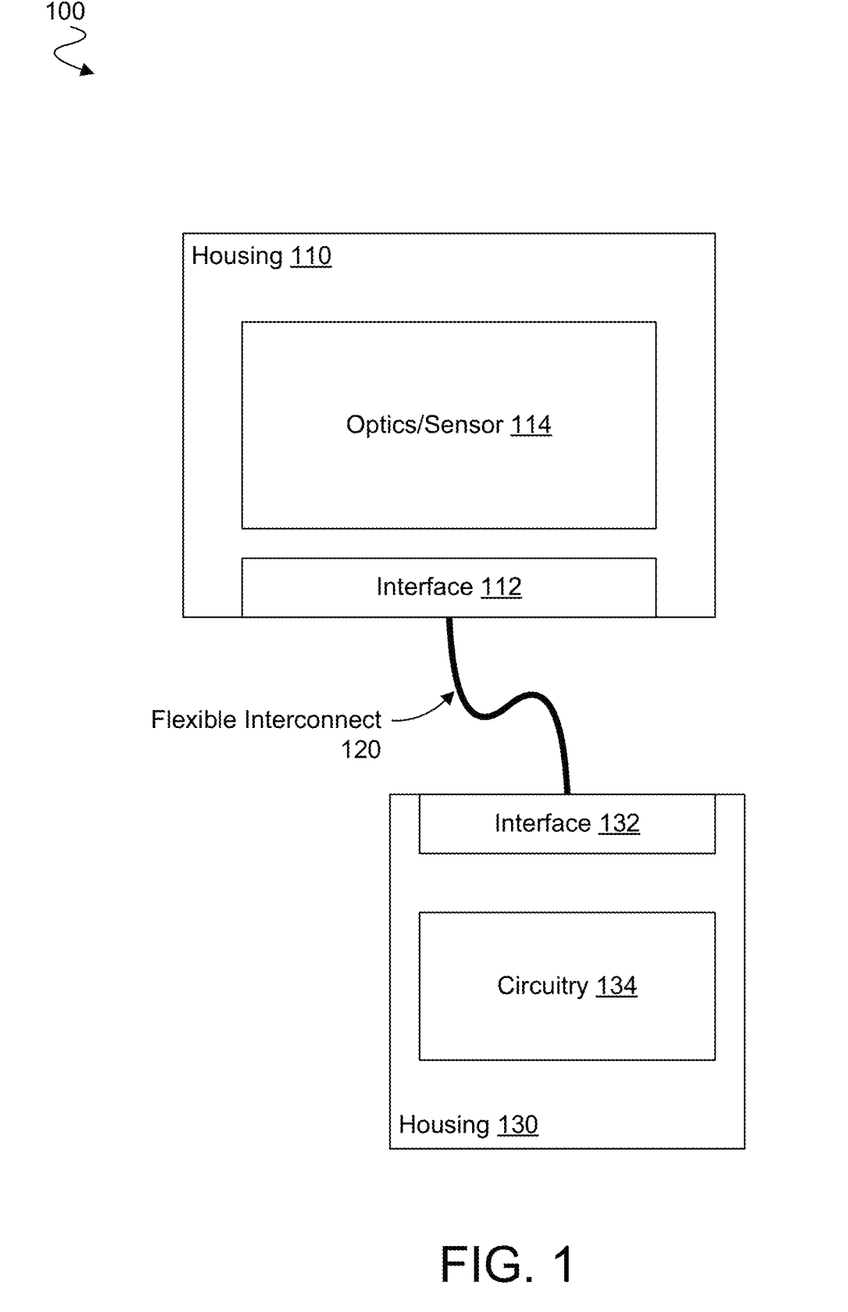
FIG. 1 is a functional block diagram showing elements of an articulated ophthalmic device in accordance with one embodiment.

FIG. 1 illustrates features of an ophthalmic device 100 including articulated structures according to an embodiment. Device 100 may accommodate implantation in a human (or other) eye—e.g. where device 100 is to perform sensing at the eye and/or to aid in sight with the eye. In the illustrative embodiment shown, device 100 includes housings 110, 130 coupled to one another via a flexible interconnect 120. An exterior of device 100 may include respective surfaces of housings 110, 130 that are biocompatible to accommodate direct contact of such surfaces with an interior of an eye. Housings 110, 130 may have different respective shapes and/or total volumes that, for example, facilitate efficient implantation of housings 110, 130 in different respective locations in an eye. In some embodiments, device 100 further comprises one or more other housings (not shown) that, for example, are flexibly coupled each to another housing of device 100.

Housings 110, 130 may have respective circuitry disposed therein. For example, an interface 112 disposed in housing 110 and an interface 132 disposed in housing 130 may include respective circuitry to facilitate one or more exchanges (e.g., including a unidirectional exchange and/or a bidirectional exchange) via interconnect 120. Such one or more exchanges may include delivery of a supply voltage, control signals, sensor data and/or the like. Interfaces 112, 132 may be hermetically sealed to protect the eye and/or operation of device 100.

One or more other components may be variously distributed among housings 110, 130, according to different embodiments. By way of illustration and not limitation, housing 110 may further have disposed therein an optical component that is to aid sight with the eye and/or a sensor component that is to sense one or more conditions in or on the eye. Such one or more components, represented as the illustrative optics/sensor 114, may operate in response to circuitry 134 disposed in housing 130. Alternatively or in addition, operation of optics/sensor 114 may generate signals to be communicated to circuitry 134 via interconnect 120.

In one embodiment, circuitry 134 includes or couples to a power source (e.g., a battery) that is to provide power for operation of optics/sensor 114. For example, the power source may power a dynamic optic of optics/sensor 114. Alternatively or in addition, circuitry 134 may provide for wireless communications between the device 100 and a remote device (not shown). In some embodiments optics/sensor 114 includes a pressure sensor disposed in or on housing 110. Data generated with such a pressure sensor may aid, for example, in clinical evaluation of an ophthalmic condition such as glaucoma. In such an embodiment, circuitry 134 may power the pressure sensor and/or process sensor data received from optics/sensor 134 via interconnect 120.

Figure 2A:
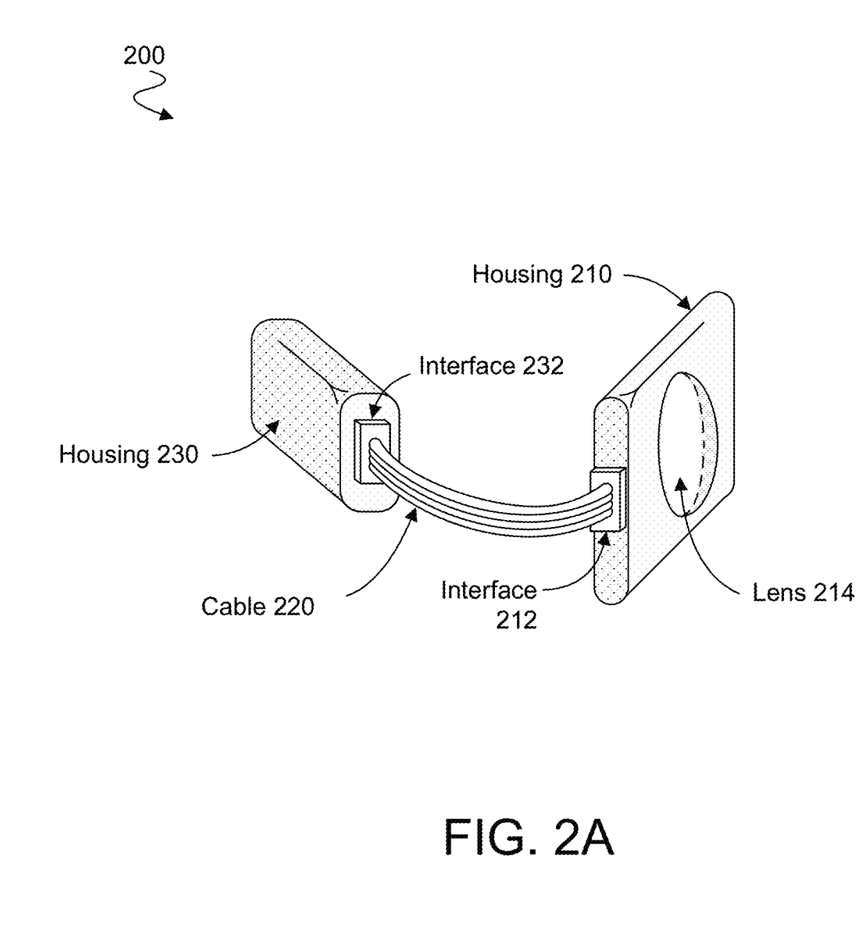
FIG. 2A is a perspective view of an articulated ophthalmic device including an accommodation lens in accordance with one embodiment.

FIG. 2A shows a perspective view of an ophthalmic device 200 including housings 210, 230 according to one illustrative embodiment. Device 200 may include some or all features of ophthalmic device 100, for example. A flexible cable 220 of device 220 may interconnect respective interfaces 212, 232 variously disposed in or on housings 210, 230. Device 200 may have a smaller cross-sectional area (e.g., one half or less) and greater flexibility at cable 220, as compared to a corresponding cross-sectional area and flexibility at either housing 210 or housing 230. At least partial flexibility of cable 220 may allow for articulation of housings 210, 230 relative to one another. For example, housings 210, 230 may be rigid and cable 220 may be semi-rigid. The respective geometries of housings 210, 230, and the scale and shapes of housings 210, 230 relative to one another, are merely illustrative and not limiting on certain embodiments.

In the illustrative embodiment shown, housing 210 forms an aperture region in which is disposed a lens 214. Although certain embodiments are not limited in this regard, lens 214 may have disposed therein a dynamic optic—e.g., wherein circuitry disposed in housing 210 aids in operation of such a dynamic optic. Such circuitry may be coupled to receive via interface 212 a supply voltage and/or control signal from circuitry that is disposed in housing 230. In response to the supply voltage and/or control signal, a level of accommodation provided with lens 214 may be selectively set (e.g., reset). Lens 214 may comprise or facilitate any of a variety of additional or alternative mechanisms to provide accommodation, according to different embodiments. Some examples of such mechanisms include liquid crystal, fluidic, electrowetting and/or the like. Although shown as being disposed in an aperture region formed by housing 210, lens 214 may itself be at least part of housing 210 or, alternatively, substitute for housing 210. For example, cable 220 may, in another embodiment, extend directly into a biocompatible material of lens 214 for coupling to circuitry disposed within lens 214.

Figure 2B:
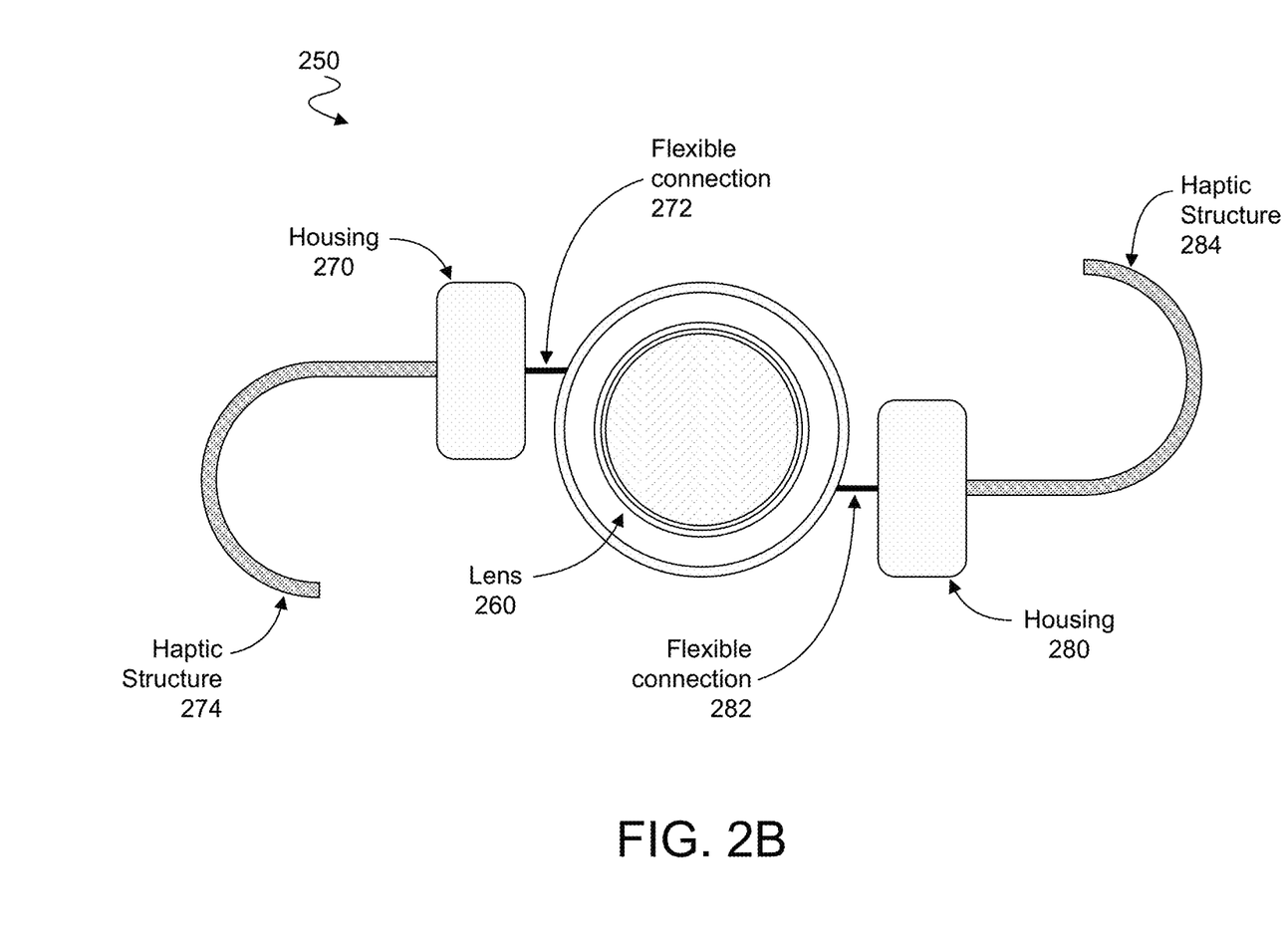
FIG. 2B is a plan view of an articulated ophthalmic device including an accommodation lens in accordance with one embodiment.

FIG. 2B illustrates elements an ophthalmic device 250 including multiple articulated housings according to another embodiment. Device 250 is one example of an embodiment—e.g., including some or all features of ophthalmic device 100—including more than two housing structures that are variously coupled to one another via flexible interconnects. In the illustrative embodiment shown, device 250 includes a lens 260 comprising a light transmissive material that serves as a housing for a dynamic optic disposed therein. Other housings 270, 280 of device 250 may be coupled to lens 260 via flexible connections 272, 282, respectively.

In the illustrative embodiment shown, device 250 includes haptic structures 274, 284 to mechanically resist movement of device 250—e.g., to aid in keeping device 250 positioned within a desired location in an eye. In such an embodiment, housings 270, 280 may be positioned each between lens 260 and a respective one of haptic structures 274, 284. However, the particular location of housings 274, 284 relative to lens 260 and haptic structures 274, 284 is merely illustrative, and not limiting on some embodiments.

Components of device 250 may be variously disposed within respective ones of housings 270, 280. Some or all such components may variously operate to facilitate the configuring of an accommodation level to be provided with lens 260. For example, integrated circuitry formed in or on lens 260 may include one or more photodetectors to detect an amount of light being transmitted to lens 260. In such an embodiment, sensor data indicating the amount of light may be communicated from lens 260 via one of connections 272, 282. In response to such sensor data, control logic disposed in one or both of housings 270, 280 may determine a new level of accommodation to be provided with lens 260. The new level of accommodation may then be communicated back to lens 260 via one of connections 272, 282.

Figure 3:
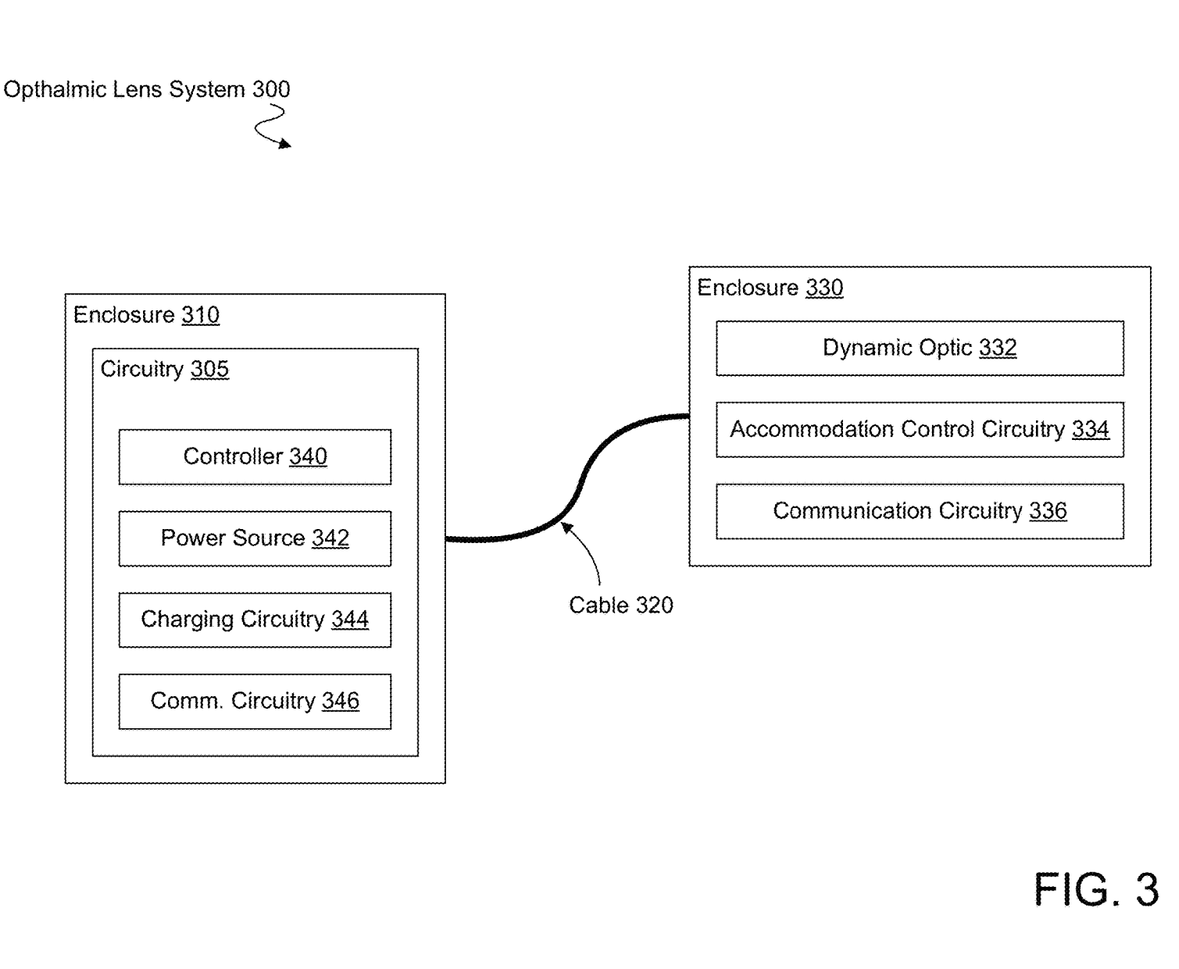
FIG. 3 is a functional block diagram of an ophthalmic lens system in accordance with one embodiment.

FIG. 3 is a functional block diagram of an ophthalmic lens system 300 including articulated housing structures, in accordance with one embodiment. Ophthalmic lens system 300 may be implemented as an intraocular lens ("IOL") capable of being implanted into an anterior chamber, posterior chamber, or other location of a user's eye. Ophthalmic lens system 300 is one example of an embodiment wherein components (e.g., including one or more of circuitry, optics, a battery, etc.) are variously disposed in—and/or variously comprise—different housings that are flexibly coupled to one another. Ophthalmic lens system 300 may include some or all of the features of one of devices 100, 200, 250, for example.

In the embodiment shown, ophthalmic lens system 300 includes enclosures 310, 330 coupled to one another via a flexible interconnect, such as the illustrative cable 320. Enclosures 310, 330 may comprise biocompatible materials each to variously seal respective components disposed therein—e.g., to provide protection for the interior of an eye in which ophthalmic lens system 300 is to be implanted. Some enclosure material may be optically transmissive (e.g., transparent, clear, etc.), in an embodiment. For example, some or all of enclosure 330 may be implemented as a silicon enclosure, or with any of other hermetically sealable materials. Of course, other optically transmissive and biocompatible materials may be used. Cable 320 may also include, or be formed in, an exterior sheathing material that is similarly biocompatible.

Enclosure 310 may have disposed therein circuitry 305 including, for example, one or more of a controller 340, power source 342, charging circuitry 344, and communication circuitry 346. Additionally or alternatively, enclosure 330 may include a dynamic optic 332, accommodation control circuitry 334 and communication circuitry 336. However, any of a variety of other distributions of components in respective ones of enclosures 310, 330 may be provided, according to different embodiments.

Controller 340 may include circuit logic that coordinates the operation of other components of ophthalmic lens system 300. Controller 340 may be implemented as hardware logic (e.g., application specific integrated circuit, field programmable gate array, etc.), software/firmware logic executed on a general purpose microcontroller, or a combination of both hardware and software/firmware logic. Power source 342 may be implemented using a variety of power storage devices including a rechargeable battery and/or capacitive elements. Charging circuitry 344, coupled to provide charging of power source 342, may include an inductive charging element, a photovoltaic element, a microelectromechanical systems ("MEMS") charging unit that uses natural motion to generate a current, or otherwise.

Communication circuitry 346 and communication circuitry 336 may exchange with one another, via cable 320, a supply voltage, control signaling, sensor data and/or the like. For example, communication circuitry 346 may be coupled to exchange control signaling with controller 340. Alternatively or in addition, communication circuitry 336 may be coupled to similarly exchange control signaling with accommodation control circuitry 334. Based on such exchanges, controller 340 may control a level of accommodation provided by dynamic optic 332. In one embodiment, one or each of communication circuitry 346 and communication circuitry 336 includes mechanisms to provide for wireless communication between ophthalmic lens system 300 and a remote device (not shown). Such mechanisms may include, for example, a passive backscatter antenna (e.g., RFID tag) or an active antenna if power budgets permit.

Dynamic optic 332 may be centrally positioned in or on enclosure 330 (or alternatively, positioned in an aperture region formed by enclosure)—e.g., to affect an optical power of ophthalmic lens system 300 in a user's center of vision. In various embodiments, dynamic optic 332 operates by changing its optical power under the influence of accommodation control circuitry 334 (for example, responsive to controller 340). By changing the optical power of dynamic optic 332, the net optical power of ophthalmic lens system 300 may be altered, thereby applying controllable accommodation. Dynamic optic 332 may be implemented using a variety of different dynamic optic technologies. For example, dynamic optic 332 may be implemented using a layer of a liquid crystal material (e.g., nematic, twisted nematic, cholesteric, or blue phase liquid crystal) disposed within a material that is disposed in or comprises enclosure 330. Liquid crystalline materials are one example of an effective technology, and may be adapted to achieve a shift in refractive index greater than 0.2 in response to an applied voltage of less than 5.0 Volts. Such a shift in refractive index is capable of providing a level of accommodation to correct near vision in presbyopic patients. In other embodiments, dynamic optic 332 may be implemented using other types of dynamic optical materials such as electro-optic materials that vary refractive index in the presence of an applied electric field. Dynamic optic 332 may be a distinct device embedded within enclosure 330, or a bulk material having a controllable refractive index. In yet another embodiment, dynamic optic 332 may be implemented using a deformable lens structure that changes shape under the influence of an electrical signal. In yet another embodiment, dynamic optic 332 may be implemented using a fluid lens whereby electrowetting or microfluidics are used to alter optical power. Accordingly, the optical power of ophthalmic lens system 300 may be controlled by accommodation control circuitry 334 with the application of electric signals via one or more electrodes extending from accommodation control circuitry 334 to dynamic optic 332.

Figure 4:
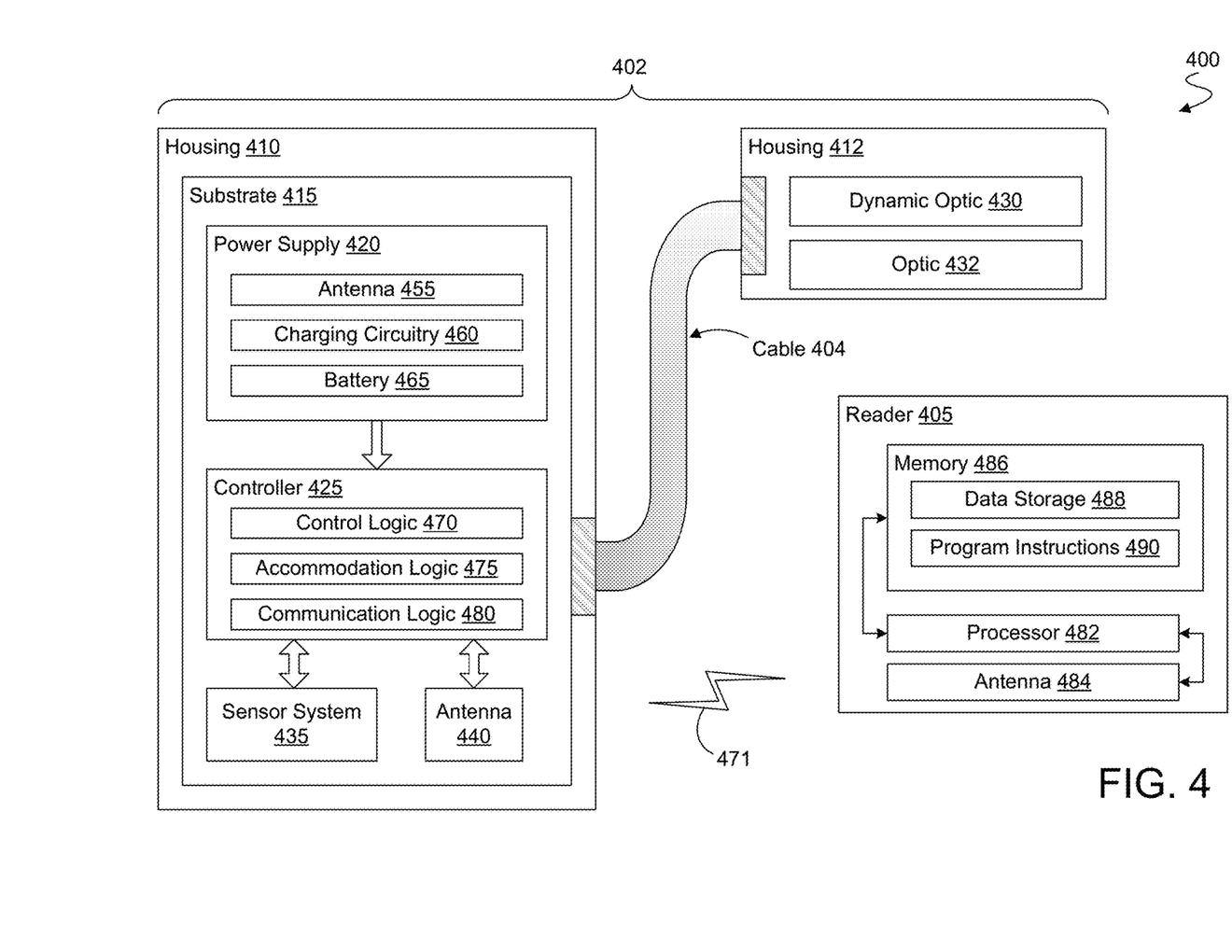
FIG. 4 is a functional block diagram of a system to exchange communications between an articulated ophthalmic device and an external reader, in accordance with an embodiment.

FIG. 4 is a functional block diagram of a system 400 for exchanging communications between an implantable ophthalmic device 402 and an external reader 405, in accordance with an embodiment of the disclosure. Device 402 may include multiple housing structures that are flexibly coupled to one another. For example, device 402 may include some or all of the features of one of devices 100, 200, 250 or of system 300. In the illustrative embodiment shown, device 402 includes housings 410, 412 coupled to one another via a flexible cable 404.

An exposed portion of device 402 may include housings 410, 412 formed to be implanted within an eye. The exposed portion of device 402 may also include cable 404 or a flexible medium in which is disposed cable 404. For example, an exterior surface of device 402 may be formed by a biocompatible hydrogel, silicone, hydrophobic acrylic, fluorinated polymethacrylate and/or the like. Some embodiments are not limited to a particular biocompatible material of housings 410, 412 (and/or of cable 404), and any of a variety of conventional biocompatible materials may be adapted for incorporation into an ophthalmic device, according to certain embodiments.

A substrate 415 may be embedded within or surrounded by housing 410 to provide a mounting surface for circuitry, such as the illustrative power supply 420, controller 425, sensor system 435, antenna 440, and various interconnects. Housing 412 may include or have disposed therein other components such as the illustrative optic 432 (e.g., including a lens structure) and a dynamic optic 430. However, any of a variety of other distributions of components in respective ones of housings 410, 412 may be provided, according to different embodiments.

The illustrated embodiment of power supply 420 includes an energy harvesting antenna 455, charging circuitry 460, and a battery 465. The illustrated embodiment of controller 425 includes control logic 470, accommodation logic 475, and communication logic 480. The illustrated embodiment of reader 405 includes a processor 482, an antenna 484, and memory 486. The illustrated embodiment of memory 486 includes data storage 488 and program instructions 490.

Controller 425 may be coupled to receive feedback control signals from sensor system 435 and further coupled to operate dynamic optic 430. Power supply 420 may supply operating voltages to the controller 425 and/or the dynamic optic 430. Antenna 440 may be operated by the controller 425 to communicate information to and/or from device 402. In one embodiment, antenna 440, controller 425, power supply 420, and sensor system 435 are all situated on the embedded substrate 415. Because device 402 includes electronics and is configured to be implanted within an eye, it is also variously referred to herein as an implantable ophthalmic device or an intraocular device.

To aid in accommodation and/or to facilitate implantation in the eye, optic 432 (and/or part of housing 412) may have a concave surface. While implanted, an outward-facing surface of optic 432 may have a convex curvature. For example, optic 432 may be a substantially transparent curved disk shaped similarly to a contact lens. Housings 410, 412 may include one or more biocompatible materials, such as those employed for use in conventional intraocular devices. Housings 410, 412 may optionally be formed in part from such biocompatible materials or may include an outer coating with such biocompatible materials. In some instances, optic 432 (and/or part of housing 412) may be shaped to provide a predetermined, vision-correcting optical power, such as can be provided by a contact lens.

Substrate 415 includes one or more surfaces suitable for mounting the sensor system 435, controller 425, power supply 420, and antenna 440. Substrate 415 may be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) may be patterned on substrate 415 to form circuitry, electrodes, etc. For example, antenna 440 may be formed by depositing a pattern of gold or another conductive material on substrate 415. Similarly, interconnects 445 and 450 may be formed by depositing suitable patterns of conductive materials on substrate 415. A combination of resists, masks, and deposition techniques may be employed to pattern materials on substrate 415. Substrate 415 may be a relatively rigid material, such as polyethylene terephthalate ("PET") or another material sufficient to structurally support the circuitry and/or electronics within housing 410. Housing 410 may alternatively include an arrangement of multiple substrates rather than a single substrate. For example, controller 425 and power supply 420 may be mounted to one substrate, while antenna 440 and sensor system 435 are mounted to another substrate and the two may be electrically connected via interconnects.

In some embodiments, dynamic optic 430 is centrally positioned in optic 432 (and/or housing 412) to provide optical accommodation to light being transmitted through both the eye and a center of optic 432. In some embodiments, device 402 further comprises one or more sensors (not shown)—e.g., one or more discrete photodetector sensors that are distributed in or on housing 412 to sense eyelid overlap. Although certain embodiments are not limited in this regard, sensor system 435 (and/or a sensor disposed in or on housing 412) may include one or more sensors to detect a pressure in the eye.

In the illustrated embodiment, power supply 420 includes a battery 465 to power the various embedded electronics, including controller 425. Battery 465 may be inductively charged by charging circuitry 460 and energy harvesting antenna 455. In one embodiment, antenna 440 and energy harvesting antenna 455 are independent antennae, which serve their respective functions of energy harvesting and communications. In another embodiment, energy harvesting antenna 455 and antenna 440 are the same physical antenna that provide respective functions for time-shared inductive charging and wireless communications with reader 405. Additionally or alternatively, power supply 420 may include a solar cell ("photovoltaic cell") to capture energy from incoming ultraviolet, visible, and/or infrared radiation. Furthermore, an inertial power scavenging system may be included to capture energy from ambient vibrations.

Charging circuitry 460 may include a rectifier/regulator to condition the captured energy for charging battery 465 or directly power controller 425 without battery 465. Charging circuitry 460 may also include one or more energy storage devices to mitigate high frequency variations in energy harvesting antenna 455. For example, one or more energy storage devices (e.g., a capacitor, an inductor, etc.) may be connected to function as a low-pass filter.

Controller 425 contains logic to choreograph the operation of the other embedded components. Control logic 470 controls the general operation of device 402, including providing a logical user interface, power control functionality, etc. Accommodation logic 475 includes logic for monitoring feedback signals from sensor system 435—e.g., determining the current gaze direction or focal distance of the user, and manipulating dynamic optic 430 in response to provide the appropriate level of accommodation. The auto-accommodation may be implemented in real-time based upon feedback from the gaze tracking, or permit user control to select specific accommodation regimes (e.g., including full accommodation for near-vision tasks such as reading and un-accommodated for distance vision tasks, etc.). Communication logic 480 provides communication protocols for wireless communication with reader 405 via antenna 440. In one embodiment, communication logic 480 provides backscatter communication via antenna 440 when in the presence of an electromagnetic field 471 output from reader 405. In one embodiment, communication logic 480 operates as a smart wireless radio-frequency identification ("RFID") tag that modulates the impedance of antenna 440 for backscatter wireless communications. The various logic modules of controller 425 may be implemented in software/firmware executed on a general purpose microprocessor, in hardware (e.g., application specific integrated circuit), or a combination of both.

Ophthalmic device 402 may include various other embedded electronics and logic modules. For example, a light source or pixel array may be included in optic 432 to provide visible feedback to the user. An accelerometer or gyroscope may be included to provide positional, rotational, directional or acceleration feedback information to controller 425.

It is noted that the block diagram shown in FIG. 4 is described in connection with functional modules for convenience in description, but does not necessarily connote physical organization. Rather, embodiments of device 402 may be arranged with one or more of the functional modules ("sub-systems") implemented in a single chip, multiple chips, in one or more integrated circuits, or otherwise.

External reader 405 includes an antenna 484 (or group of more than one antennae) to send and receive wireless signals 471 to and from device 402. External reader 405 also includes a computing system with a processor 482 in communication with a memory 486. Memory 486 is a non-transitory computer-readable medium that may include, without limitation, magnetic disks, optical disks, organic memory, and/or any other volatile (e.g. RAM) or non-volatile (e.g. ROM) storage system readable by the processor 482. Memory 486 may include a data storage 488 to store indications of data, such as data logs (e.g., user logs), program settings (e.g., to adjust behavior of device 402 and/or external reader 405), etc. Memory 486 may also include program instructions 490 for execution by processor 482 to cause the external reader 405 to perform processes specified by the instructions 490. For example, program instructions 490 may cause external reader 405 to provide a user interface that allows for retrieving information communicated from device 402 or allows transmitting information to device 402 to program or otherwise select operational modes of device 402. External reader 405 may also include one or more hardware components for operating antenna 484 to send and receive wireless signals 471 to and from device 402.

External reader 405 may be a smart phone, digital assistant, or other portable computing device with wireless connectivity sufficient to provide the wireless communication link 471. External reader 405 may also be implemented as an antenna module that can be plugged in to a portable computing device, such as in an example where the communication link 471 operates at carrier frequencies not commonly employed in portable computing devices. In some instances, external reader 405 is a special-purpose device configured to be worn relatively near a wearer's eye to allow the wireless communication link 471 to operate with a low power budget. For example, the external reader 405 may be integrated in a piece of jewelry such as a necklace, earing, etc. or integrated in an article of clothing worn near the head, such as a hat, headband, etc.

Figure 5:
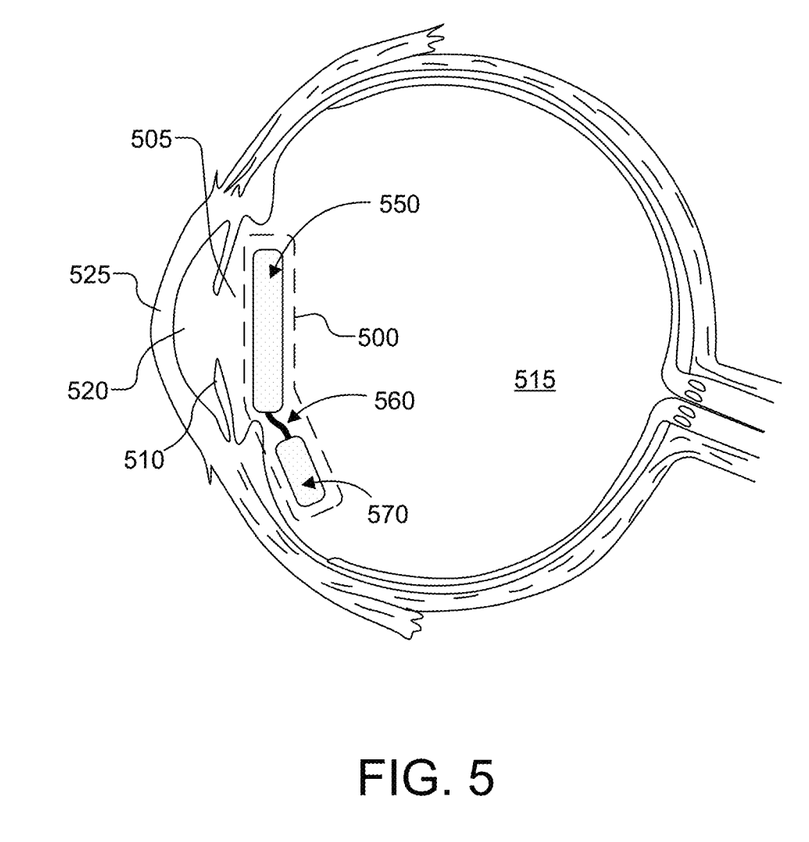
FIG. 5 is a cross-sectional illustration of an eye with an implanted intraocular device in accordance with an embodiment.

FIG. 5 is a cross-sectional illustration of an eye 515 with an implanted IOL system 500 including articulated housing structures in accordance with one embodiment. IOL system 500 may include some or all of the features of one of devices 100, 200, 250, 402 or of system 300, for example. In the illustrative embodiment shown, device 500 includes housings 550, 570 coupled to one another via a flexible connection 560. The particular arrangement of housings 550, 570 relative to one another is merely illustrative, and not limiting on some embodiments. An interconnect such as flexible connection 560 may be flexed during implantation in an eye—e.g., where flexible connection 560 returns to some relatively low stress shape after such implantation is complete. IOL system 500 is illustrated as being implanted within the posterior chamber 505 behind iris 510. However, IOL system 500 may be implanted into other locations, as well, such as anterior chamber 520 disposed between iris 510 and cornea 525.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize. These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An intraocular device for implantation in an eye, the intraocular device comprising:
   discrete housing structures including a first housing, a second housing, and a third housing, wherein the discrete housing structures are each rigid encasements physically separated and spaced apart from each other, and wherein the first housing is positioned between the second housing and the third housing;
   a first and a second flexible interconnect to respectively couple the second and the third housings to the first housing, wherein the first flexible interconnect is coupled between the first housing and the second housing, wherein the second flexible interconnect is coupled between the first housing and the third housing, wherein the first flexible interconnect provides articulation of the second housing relative to the first housing, and wherein the second flexible interconnect provides articulation of the third housing relative to the first housing;
   a first and a second haptic structure extending from the second housing and the third housing respectively, each to resist movement of the intraocular device when implanted in the eye, wherein a first proximal end of the first haptic structure and the first flexible interconnect are positioned on opposite sides of the second housing, and wherein a second proximal end of the second haptic structure and the second flexible interconnect are positioned on opposite sides of the third housing;
   a dynamic optic at least partially disposed within the first housing, wherein the dynamic optic provides a level of accommodation for the eye;
   a first component disposed within the second housing, wherein the first component is electrically coupled to the first housing via the first flexible interconnect; and
   a second component disposed within the third housing, wherein the second component is electrically coupled to the first housing via the second flexible interconnect.

2. The intraocular device of claim 1, further comprising:
   a plurality of discrete sensors distributed in or on the first housing to generate a feedback control signal indicative of eyelid overlap,
   wherein the first component includes a controller coupled to receive the feedback control signal via the first flexible interconnect, and wherein the controller is configured to operate the dynamic optic responsive to the feedback control signal for providing real-time auto-accommodation.

3. The intraocular device of claim 1, wherein the first haptic structure has a first width greater than a width of the first flexible interconnect, and wherein the second haptic structure has a second width greater than a width of the second flexible interconnect.

4. The intraocular device of claim 1,
wherein the first component includes a battery coupled to a controller, each disposed on a shared substrate disposed within the second housing, wherein the controller is configured to provide a supply voltage to power the dynamic optic via the first flexible interconnect.

5. The intraocular device of claim 1, further comprising:
a pressure sensor disposed at least partially within the first housing, and
wherein the first component includes a power source, disposed within the second housing, coupled to the pressure sensor via the first flexible interconnect to power operation of the pressure sensor.

6. The intraocular device of claim 1, further comprising:
wireless communication logic disposed within at least one of the first housing, the second housing, or the third housing, wherein the wireless communication logic is adapted to exchange wireless communications.

7. The intraocular device of claim 1, wherein a total volume of the first housing is different than a total volume of the second housing.

8. The intraocular device of claim 1, wherein each of the discrete housing structures are hermetically sealed and include a coating of a biocompatible material.

9. The intraocular device of claim 1, wherein the first flexible interconnect and the second flexible interconnect are less rigid than the first housing, the second housing, and the third housing.

10. The intraocular device of claim 1, wherein a first width of the first haptic structure and a second width of the second haptic structure is less than a width of at least one of the first housing, the second housing, or the third housing.

11. The intraocular device of claim 1, wherein the first housing is disposed between the first flexible interconnect and the second flexible interconnect, wherein the second housing is disposed between the first haptic structure and the first flexible interconnect, and wherein the third housing is disposed between the second flexible interconnect and the second haptic structure.

12. The intraocular device of claim 1, wherein the second housing and the third housing each include an outer coating of a biocompatible material.

* * * * *